United States Patent [19]

Moren et al.

[11] Patent Number: 5,364,693

[45] Date of Patent: Nov. 15, 1994

[54] ORTHOPEDIC SUPPORT MATERIALS

[75] Inventors: Dean M. Moren, North St. Paul; Dean A. Ersfeld, Maplewood, both of Minn.

[73] Assignee: Minnesota Mining and Manufacturing Company, St. Paul, Minn.

[21] Appl. No.: 8,678

[22] Filed: Jan. 25, 1993

[51] Int. Cl.⁵ .............................. B32B 7/00
[52] U.S. Cl. .................... 428/263; 428/253; 428/254; 428/260; 428/289; 428/290
[58] Field of Search ........... 428/253, 254, 260, 263, 428/289, 290

[56] References Cited

U.S. PATENT DOCUMENTS

| | | | |
|---|---|---|---|
| 2,809,184 | 10/1957 | Langer | 260/47 |
| 2,946,756 | 7/1960 | Wheelock et al. | 260/2 |
| 3,027,336 | 3/1962 | Gotz et al. | 260/2.5 |
| 3,216,964 | 11/1965 | Brubaker et al. | 260/31.8 |
| 3,324,075 | 6/1967 | Burak | 260/41.5 |
| 3,475,371 | 10/1969 | Stewart et al. | 260/45.7 |
| 3,630,917 | 12/1971 | McCord | 252/78 |
| 3,694,399 | 9/1972 | Schwarz | 260/41 B |
| 3,780,132 | 12/1973 | Lohr | 260/831 |
| 4,143,013 | 3/1979 | Jenkinson et al. | 260/29.1 B |
| 4,283,387 | 8/1981 | Young et al. | 424/78 |
| 4,335,158 | 6/1982 | Beede et al. | 427/2 |
| 4,411,262 | 10/1983 | von Bonin et al. | 128/90 |
| 4,473,671 | 9/1984 | Green | 523/105 |
| 4,480,072 | 10/1984 | Mallon | 525/61 |
| 4,502,479 | 3/1985 | Garwood | 128/90 |
| 4,570,622 | 2/1986 | von Bonin et al. | 128/90 |
| 4,584,280 | 4/1986 | Nanao et al. | 501/80 |
| 4,593,068 | 6/1986 | Hirose et al. | 525/100 |
| 4,609,578 | 9/1986 | Reed | 427/289 |
| 4,628,076 | 12/1986 | Chang et al. | 525/440 |
| 4,667,661 | 5/1987 | Scholz et al. | 128/90 |
| 4,672,956 | 6/1987 | Potter et al. | 128/90 |
| 4,774,937 | 10/1988 | Scholz et al. | 128/90 |
| 4,788,164 | 11/1988 | Che et al. | 501/39 |
| 4,814,368 | 3/1989 | Stein et al. | 524/158 |
| 4,841,958 | 6/1989 | Ersfeld et al. | 128/90 |
| 4,856,502 | 8/1989 | Ersfeld et al. | 128/90 |
| 4,879,065 | 11/1989 | Sterzel | 252/600 |
| 4,882,377 | 11/1989 | Sweet et al. | 524/267 |
| 4,910,255 | 3/1990 | Wakabayashi et al. | 525/100 |
| 4,951,656 | 8/1990 | Gorka et al. | 128/90 |
| 4,977,228 | 12/1990 | Wakabayashi et al. | 528/12 |
| 5,005,566 | 4/1991 | Klintworth, Jr. | 128/90 |
| 5,041,287 | 8/1991 | Driggers et al. | 424/81 |
| 5,052,380 | 10/1991 | Polta | 128/90 |

FOREIGN PATENT DOCUMENTS 486020 5/1992 European Pat. Off. .
926037 5/1963 United Kingdom .

OTHER PUBLICATIONS

C. C. Sun and J. E. Mark, *Journal of Polymer Science; Part B; Polymer Physics*, vol. 25, 1561–1564 (1987).

*Primary Examiner*—James J. Bell
*Attorney, Agent, or Firm*—Gary L. Griswold; Walter N. Kirn; F. Andrew Ubel

[57] ABSTRACT

The present invention provides a water-curable resin composition for use in an orthopedic cast composed of a water-reactive liquid organometallic compound having at least one hydrolyzable group per molecule and a viscosity of no greater than about 100,000 centipoise under ambient conditions; and an organic polymer, having a number average molecular weight of at least about 400, mixed with the water-reactive liquid organometallic compound. Preferably, the water-reactive liquid organometallic compound is a compound of the formula $(R^1O)_x MR^2_{(y-x)}$ wherein: each $R^1$ is independently a substituted or unsubstituted $C_1$–$C_{100}$ hydrocarbon group, optionally interrupted in the backbone by 1–50 nonperoxide —O—, —S—, —C(O)—, or —N— groups; each $R^2$ is independently selected from the group consisting of hydrogen and a substituted or unsubstituted $C_1$–$C_{100}$ hydrocarbon group, optionally interrupted in the backbone by 1–50 nonperoxide —O—, —S—, —C(O)—, or —N— groups; x is an integer between 1 and y, inclusive; y is the valence of M; and M is boron, aluminum, silicon, or titanium.

38 Claims, 1 Drawing Sheet

ORTHOPEDIC SUPPORT MATERIALS

FIELD OF THE INVENTION

The present invention relates to orthopedic support materials made of a substrate impregnated with a water-curable resin composition. The invention also relates to methods of making the support materials, methods of making casts from the support materials, and the resulting products.

BACKGROUND OF THE INVENTION

While the methods, compositions, and materials presented herein can be used in a variety of applications, they are well adapted for use with respect to orthopedic support materials, such as casting tapes. Therefore, as background, characterizations of technology relating to orthopedic casting tapes and problems overcome by the present invention are provided.

Orthopedic casting tapes have been produced using curable resins coated or impregnated onto a substrate. Typically, the casting tape is stored as a roll in a water-impermeable storage pouch until needed for use. When needed, the roll of tape is removed from the pouch and contacted with water. Generally, the tape includes a resin therein that is water-curable. Thus, shortly after the tape is dipped in water, the resin will begin to cure and the tape harden. A medical practitioner applies the casting tape to a patient immediately after it has been immersed in water. Generally, resin materials are chosen that begin to cure immediately after being dipped in water, and that will harden sufficiently to resist passive motion in a joint, i.e., a wrist or ankle, in 3-5 minutes, and to be weight bearing within about 30 minutes.

Typical resin coatings utilized in conventional orthopedic casting systems include isocyanate-functional polyurethane prepolymers. Generally the resin coatings also include lubricants to facilitate unrolling, application, and molding without the resin interfering. Furthermore, they often include defoaming agents to maintain porosity while carbon dioxide is evolved during the curing process. When exposed to water, the isocyanate functional polyurethane prepolymers cure to form polyureas. In certain situations, it may be desirable to avoid or reduce the level of such reactive groups and products.

Typical substrates upon which the above resin coatings are applied to produce an orthopedic casting tape are knit fabrics prepared from glass and/or synthetic fibers. Fiberglass or other high modulus fibers contribute significant strength to the cured resin/substrate composite as well as provide a reservoir for the resin during storage and end-use application of the casting tape. Nonglass and low modulus substrates generally provide for a lower weight and more radiolucent cast. Here the strength is limited by the amount of resin that can be held by the substrate. High resin loading with materials known to date must generally be avoided, however, to prevent excessive heat build-up in the cast while it is in its early stages of cure, i.e., during hardening, as a result of the exotherm produced in the above resins. Furthermore, high resin loads with conventional resins must generally be avoided to prevent undesirable pooling of the resin. "Pooling" is the uneven distribution of the resin on the substrate as a result of the flow of resin due to gravity.

Orthopedic casting tapes of this type are described in U.S. Pat. Nos. 4,667,661 and 4,774,937 (Scholz et al.), which are owned by Minnesota Mining and Manufacturing Company of St. Paul, Minn., the assignee of the present invention. Such tapes are also commercially available from 3M Company under the tradenames Scotchcast® Plus casting tape and Scotchcast® 3 casting tape. Construction materials of this type are also described in U.S. Pat. Nos. 4,411,262 and 4,570,622 (von Bonin et al.). These materials are one-component systems containing isocyanate or alkoxysilane groups, i.e., silyl-substituted urea, biuret, and urethane derivatives.

A need exists for a water-curable resin composition that can be used in a wide variety of orthopedic support materials, whether used in combination with a fiberglass substrate or a nonglass low modulus substrate. That is, a need exists for a resin composition that can be used in large amounts, i.e., at high resin loads, without excessive heat build-up, resin pooling, and/or perceived health hazards, as well as in smaller amounts.

RELATED APPLICATIONS

Of related interest are the following U.S. Patent Applications, filed on Jan. 25, 1993 by the assignee of this invention: *Microfiber Fillers for Orthopedic Casting Tapes*—Ser. No. 08/008,755; *Microcreping of Fabrics for Orthopedic Casting Tapes*—Ser. No. 08/008,751; *Mechanically Compacted Fabrics for Orthopedic Casting Tapes*—Ser. No. 08/008,161; *Water Curable Resin Compositions*—Ser. No. 08/008,743; and *Fabric for Orthopedic Support Materials*—Ser. No. 08/004,925 which are herein incorporated by reference.

SUMMARY OF THE INVENTION

The present invention provides a water-curable resin-coated sheet, preferably useable in a water-hardenable medical dressing capable of immobilizing and/or supporting a body part. This hardenable dressing can be used in tape, sheet, film, slab, or tubular form to prepare orthopedic casts, splints, braces, supports, protective shields, orthotics, and the like. Additionally, other constructions in prefabricated shapes can be used. As used herein the terms "orthopedic support material" or "orthopedic casting material" are used to encompass any of these forms of dressings, and "cast" or "support" are used to include any of these orthopedic support structures.

The water-hardenable dressing of the present invention is composed of a substrate coated or impregnated with a water-curable multicomponent resin composition. The resin composition is stable at a temperature of about 0°-40° C. and is capable of curing upon exposure to water to form a composite material at a temperature of about 10°-100° C. It includes an organic polymer mixed, i.e., uniformly dispersed, with a water-reactive liquid organometallic compound. The organometallic compound is present in an amount of about 1-99 wt-%, based on the total weight of the resin composition.

The water-reactive liquid organometallic compound contains at least one hydrolyzable group per molecule, i.e., water-reactive groups, and preferably at least three hydrolyzable groups. The hydrolyzable groups include, halogen atoms, alkoxy groups, alkenoxy groups, carboxy groups, amino groups, amide groups, dialkylaminooxy groups, ketoxime groups

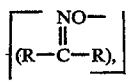

aldoxime groups

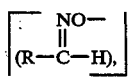

and the like. Preferably, the hydrolyzable groups are selected from the group consisting of alkoxy, alkenoxy, dialkylaminooxy, carboxy, amino, amide, ketoxime, and aldoxime. More preferably, the hydrolyzable groups are alkoxy groups such as methoxy and ethoxy.

Typically, the organometallic compounds used in the resin compositions of the present invention undergo hydrolysis on contact with water to form the corresponding metal hydroxides. These metal hydroxides generally undergo subsequent condensation reactions to form compounds having M—O—M bonds (M = metal). In this way, organometallic compounds can decompose to form an essentially inorganic reinforcing material.

Preferably, a liquid organometallic compound useful in the compositions of the present invention has a viscosity of no greater than about 100,000 centipoise under ambient conditions. The organic polymer preferably has a number average molecular weight of at least about 400. Although the organic polymer may be dispersible in the liquid organometallic compound, it is preferably soluble in the organometallic compound. As a result of this interaction (i.e., dispersion or solution), a wider variety of polymers can be used in orthopedic casting materials than has been previously possible. The resultant water-curable multicomponent resin composition has a viscosity of about 5,000–500,000 centipoise under ambient conditions, i.e., at a temperature of about 20°–30° C. and atmospheric pressure (about 1 atm). As used herein "water-curable" means that the multicomponent resin composition is capable of hardening to a rigid, semi-rigid, or flexible structure on exposure to water such that the resin composition is no longer fluid, i.e., no longer flowable. Although water-cure can occur under a variety of conditions of temperature and pressure, it advantageously occurs under ambient conditions.

The resin composition can also include an effective amount of a catalyst and other adjuvants such as slip agents, toughening agents, surfactants, fillers, tackifiers, pigments, dyes, and fragrances. As used herein "an effective amount" means an amount sufficient to provide one or more of the benefits of such an additive, as described herein.

Suitable substrates include knit, woven, and nonwoven fabrics as well as foams and other porous materials. The fabric is generally formed in rolls of various widths, generally about 1–6 inches (2.54–15.2 cm) in width. The fabric is impregnated with the water-curable multicomponent resin composition in an amount of about 1–3 times the volume of the material forming the fabric. As used herein "impregnate" refers to a condition in which the resin composition is thoroughly intermingled with, and in surrounding relation to, the fibers or filaments of the fabric. Generally, the resin composition flows into the spaces in the fabric between the fibers or filaments. Upon curing, the resin composition generally becomes bonded, physically or chemically, to the fabric, forming a composite material.

The water-reactive liquid organometallic compound having hydrolyzable groups is preferably a compound of the formula $(R^1O)_xMR^2_{(y-x)}$ (Formula I) wherein: each $R^1$ is independently a substituted or unsubstituted $C_1$-$C_{100}$ hydrocarbon group, optionally interrupted in the backbone by 1–50 nonperoxide —O—, —C(O)—, —S—, or —N— groups; each $R^2$ is independently selected from the group consisting of hydrogen and a substituted or unsubstituted $C_1$-$C_{100}$ hydrocarbon group, optionally interrupted in the backbone by 1–50 nonperoxide —O—, —C(O)—, —S—, or —N— groups; x is an integer between 1 and y, inclusive; y is the valence of M; and M is selected from the group consisting of boron, aluminum, silicon, and titanium. Preferably x=y, and more preferably x=3.

Preferably, the uncured resin compositions of the present invention are substantially free of low-molecular weight monomers, dimers, etc., i.e., those molecules under a molecular weight of about 400, particularly those containing isocyanate functionality. In certain situations, the uncured resin compositions are substantially free of all isocyanate-containing polymers. That is, the resin compositions include a substantially isocyanate-free organic polymer because the resin compositions of the present invention make the presence of isocyanate monomers/dimers, etc. unnecessary to obtain a resin of workable viscosity. Most preferably, the isocyanate-free organic polymer is an addition polymer made from ethylenically unsaturated monomers, such as butadiene, styrene, isobutyl methacrylate, maleic anhydride, vinyl triethoxysilane, 3-(trimethoxysilyl)propyl methacrylate, and mixtures thereof.

In the context of the present invention with respect to Formula I, the term "hydrocarbon" means an aromatic, heterocyclic, saturated or unsaturated linear, branched, or cyclic group. This term is used to encompass alkyl and vinyl groups, for example. Also included within the meaning of the term "hydrocarbon" as used herein are acyl groups and poly(alkylene oxide) groups. The term "heterocyclic" means a mono- or polynuclear saturated or unsaturated cyclic radical containing carbons and one or more heteroatoms such as nitrogen, oxygen, phosphorus, silicon, or sulfur or a combination thereof in the ring or rings. The term "alkyl" means a monovalent residue remaining after removal of a hydrogen atom from a linear or branched chain hydrocarbon. The term "cycloalkyl" means a monovalent residue remaining after removal of a hydrogen atom from a saturated cyclic hydrocarbon. The term "aromatic" or "aryl" means a monovalent residue remaining after removal of a hydrogen atom from an aromatic compound (single ring and multi- or fused-ring) including substituted aromatics such as lower alkaryl and aralkyl groups, lower alkoxy, N,N-di(lower alkyl)amino, nitro, cyano, halo, and lower alkyl carboxylic acid ester, wherein "lower" means a group having 1–4 carbon atoms. The term "acyl" means a monovalent organic residue remaining after removal of the OH from an aryl, alkyl, or cycloalkyl carboxylic acid. The term "alkenyl" means monovalent residue remaining after removal of a hydrogen atom from a linear or branched chain hydrocarbon containing at least one carbon-carbon double bond.

BRIEF DESCRIPTION OF THE INVENTION

FIG. 1 is a schematic representation of the casting material of the present invention shown wrapped in position for cure.

DETAILED DESCRIPTION OF THE INVENTION

Figure 1:
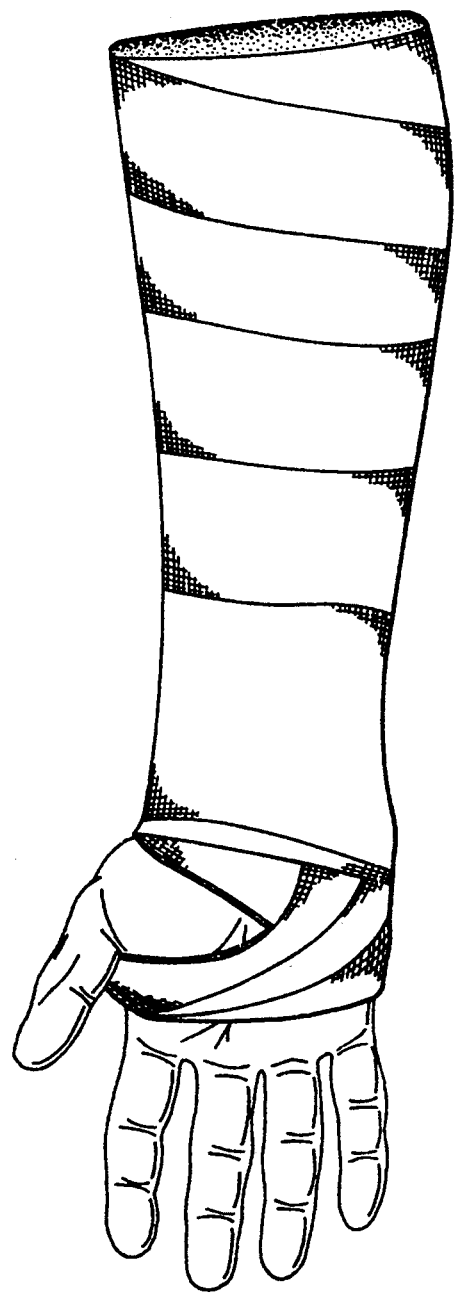

As indicated above, conventional orthopedic casting materials generally comprise a substrate having polyurethane prepolymer resins distributed therein. Upon exposure to water, the resin will cure with the evolution of heat forming a hard tough polyurea urethane. Such compositions are described for example in U.S. Pat. No. 4,502,479 (Garwood et al.), U.S. Pat. No. 4,619,578 (Reed), U.S. Pat. No. 4,667,661 (Scholz et al.), and U.S. Pat. No. 4,774,937 (Scholz et al.), each of these references being incorporated herein by reference. The present invention provides generally fast-curing coated substrates, particularly at room temperature, that remain cool during cure.

Suitable resin compositions for use in the orthopedic casting materials, e.g., tapes, of the present invention preferably have the following properties: (1) substantial storage life; (2) low toxicity; (3) appropriate viscosity and flow characteristics that allow it to coat the substrate and remain in place, on and within the substrate, while in storage and during cure; (4) water-curable, i.e., curable upon exposure to moisture in the air, upon immersing in water, or through some similar action; (5) fast cure rate, i.e., set-up within 3–5 minutes to the shape of the body part, and cure to form a weight-bearing cast within a period of about 30 minutes to several hours; (6) cure to a relatively strong, tough, and long lasting cast such that the cast is sufficiently strong (whether flexible, semi-rigid, or rigid) to support a fractured limb; (7) cure without the generation of substantial heat that can harm the patient; (8) cure to a substantially waterproof cast, i.e., a cast that will not soften or delaminate upon contact with water after cure; (9) cure without undesirable amounts of bloom from various additives included therein; (10) cure to form a cast that can be readily removed without discomfort to the patient; (11) cure with little shrinkage of the cast; (12) nontacky upon contact with water; (13) minimal or nonoffensive smell; (14) free of offensive or noxious organic solvents; (15) reasonable work life such that there is a reasonable period of time in which to mold the material to the limb; (16) reasonable flexibility such that the material readily assumes the shape of the limb during application; and (17) does not cause skin irritation as a result of chemical irritation.

The present invention concerns the development and identification of such a resin composition. Preferably, such a composition is further characterized by the substantial avoidance therein of low-molecular weight materials, i.e., having a molecular weight less than about 400, such as those monomers, dimers, etc. containing isocyanate groups. Furthermore, in certain situations, the compositions of the present invention are substantially free of all isocyanate-containing polymers because such groups are unnecessary to obtain a resin of workable viscosity. Thus, the present invention provides an alternative to conventional isocyanate-based coating materials.

Curable resin compositions for use in orthopedic casting tapes according to the present invention generally include compositions composed of: (a) a water-reactive liquid organometallic compound having at least one hydrolyzable group; mixed, i.e., uniformly dispersed, with (b) an organic polymer having a number average molecular weight of at least about 400. The organic polymer is stably dispersible in the liquid organometallic compound, or the organometallic compound is stably dispersible within the organic polymer, depending upon the relative amounts. Preferably, the liquid organometallic compound acts as a solvent for the resin composition with the organic polymer soluble therein. The organic polymer will remain dispersed within the organometallic compound, or vice versa depending upon the relative amounts of the two components, after cure. Alternatively, the organic polymer and organometallic compound may react with each other upon cure.

Thus, in preferred embodiments the liquid organometallic compound operates as a solvent for the polymer in the resin composition, as well as being a reactant in the system. In this way, the resin compositions of the present invention does not require the use of any organic solvents or dispersants, such as, for example, methanol, dioxane, tetrahydrofuran, 2-ethoxyethanol, or 2-methoxyethanol. Thus, the water-curable resin compositions of the present invention contain substantially no organic solvent, i.e., they are substantially free of organic solvents.

The water-reactive organometallic compound is used in the present multicomponent resin compositions in an amount of about 1–99 wt-%, based on the total weight of the resin composition. Similarly, the organic polymer is used in an amount of about 1–99 wt-%. Preferably, the organometallic compound is present in an amount of about 5–50 wt-%, and more preferably in an amount of about 15–30 wt-%. Preferably, the organic polymer is present in an amount of about 50–95 wt-%, and more preferably in an amount of about 70–85 wt-%.

The multicomponent resin composition, i.e., the combination of water-reactive liquid organometallic compound and organic polymer, is flowable such that it coats a substrate and remains in place, on and within the substrate, while in storage and during cure. Generally, it has a viscosity of no greater than about 500,000 centipoise (cps) and at least about 5,000 cps, i.e., a viscosity of about 5,000–500,000 cps. Preferably for use as an impregnant for typical fabrics employed as orthopedic casting tapes, the resin composition of the present invention has a viscosity of no greater than about 300,000 cps, more preferably no greater than about 100,000 cps, and most preferably no greater than about 70,000 cps. Although generally, the resin composition of the present invention has a viscosity of at least about 5,000 cps, preferably the viscosity is at least about 10,000 cps, under ambient conditions, i.e., room temperature (about 20°–30° C.) and atmospheric pressure (about 1 atm).

Control of the viscosity of the resin composition is important for many applications and is dependent upon factors such as polymer composition and molecular weight, as well as the relative amounts of the organometallic liquid and the organic polymer. Generally, the higher the molecular weight of the organic polymer and the higher the organic polymer to organometallic liquid ratio, the higher the composition viscosity. Also, the higher the amount of a filler, the higher the composition viscosity.

A resin composition of low viscosity is desirable, for example, when the composition is to be sprayed onto a substrate. In contrast, a resin composition of high viscosity is desirable, for example, when the composition is to be used as a putty that must be conformable yet maintain its shape as it cures. A moderate viscosity may be desirable if, for example, the composition is to be applied to a substrate by brush.

The resin composition viscosity is also affected by the type of organic polymer. That is, the resin composition viscosity is affected by hydrogen bonding moieties, such as amides, urethanes, and alcohols, by crystalline moieties, such as stearate and polycaprolactone, and by other molecularly associating species, such as fluorocarbons. Moieties such as these may be attached to the organic polymer in a side-chain fashion or they may be incorporated directly into the polymer backbone.

Upon hardening, the resin compositions of the present invention generate little heat, thereby lessening the possibility of harm to the patient upon curing of the resin. They also cure without extensive foaming and evolution of $CO_2$. The practical result of the generation of little heat and $CO_2$ upon curing is that the casting material can include a larger amount of resin, i.e., there can be a higher coating weight on the substrate. The larger amount of resin provides additional strength to the resultant orthopedic support. This is of particular utility when a low modulus organic substrate is used, such as a polyester fabric, which provides lighter weight casts and increased radiolucency. Also, the cured compositions retain most of their strength in the presence of water and heat.

The Organometallic Compound

Suitable organometallic compounds for use in the resin compositions of the present invention are liquid under ambient conditions, i.e., room temperature (20°–30° C.) and atmospheric pressure (about 1 atm). They have a viscosity of no greater than about 100,000 cps, preferably no greater than about 10,000 cps, more preferably no greater than about 3,000 cps, and most preferably no greater than about 1,000 cps. They also contain hydrolyzable groups, i.e., groups that react with water. Each molecule of the organometallic compound contains at least one hydrolyzable group, and preferably at least three hydrolyzable groups. A hydrolyzable group functionality, i.e., the number of groups per molecule, of three results in faster cure and better crosslink density of the cured product.

The hydrolyzable groups include, halogen atoms, alkoxy groups, carboxy groups, amino groups, amide groups, dialkylaminooxy groups, ketoxime groups, aldoxime groups, and the like. Preferably, the hydrolyzable groups are selected from the group consisting of alkoxy, alkenoxy, carboxy, amino, amide, dialkylaminooxy, ketoxime, and aldoxime. More preferably, the hydrolyzable groups are alkoxy groups, such as methoxy and ethoxy, at least because they are readily hydrolyzed, produce acceptable odors, and have low toxicity, good shelf stability, and high controllable reactivity. Once they react with water, the resultant compounds typically contain condensable hydroxide groups. Thus, the hydrolyzed organometallic compounds are then capable of condensing to form higher molecular weight species, which ultimately solidify.

Although not intending to be limited to any particular theory, upon hydrolysis and condensation, the organometallic compounds suitable for use in the present invention are thought to react either to form discrete reinforcing solid domains within an organic polymer matrix, or to form an organometallic polymer matrix. The organometallic polymer matrix could surround discrete organic polymer domains or it could be intertwined with an organic polymer matrix to form an interpenetrating network. Whether organometallic solid domains or organometallic polymer matrices are formed may depend on the type of organometallic compound chosen, on the amount used relative to the amount of organic polymer in the resin composition, and on any catalyst used to promote the reaction. For example, if the organometallic compound is an organoborate, upon hydrolysis it is believed that solid domains of boric acid are formed within the solidified organic polymeric matrix. If, however, the organometallic compound contains silicon and a sufficient amount is used, upon hydrolysis a silicon-containing polymeric matrix, such as a silica matrix may be formed. If formed, such a matrix may be intertwined with the solidified organic polymeric matrix.

Thus, the organometallic compound after hydrolysis could in theory contribute to the strength of the product, by acting as a reinforcing filler in the organic polymeric matrix, or by forming a polymeric matrix. In preferred embodiments, the organometallic compound cures to form a covalent interaction with the organic polymer. In sum, the organometallic liquid compound, preferably acting as the solvent in the resin composition, is a reactant, capable of forming a filler and/or a crosslinked matrix, and it may participate in crosslinking between organic polymer chains.

In general, a preferred liquid organometallic compound has the general formula (Formula I):

$$(R^1O)_xMR^2_{(y-x)}$$

wherein:
each $R^1$ is independently a substituted or unsubstituted $C_1$–$C_{100}$ hydrocarbon group, optionally interrupted in the backbone by 1–50 nonperoxide —O—, —C(O)—, —S—, or —N— groups;
each $R^2$ is independently selected from the group consisting of hydrogen and a substituted or unsubstituted $C_1$–$C_{100}$ hydrocarbon group, optionally interrupted in the backbone by 1–50 nonperoxide —O—, —C(O)—, —S—, or —N— groups;
x is an integer between 1 and y, inclusive;
y is the valence of M; and
M is selected from the group consisting of boron, aluminum, silicon, and titanium.

Herein, when it is said that "each" $R^1$ or $R^2$ is "independently" some substituent group, it is meant that generally there is no requirement that all $R^1$ groups be the same, nor is there a requirement that all $R^2$ groups be the same. With respect to y, the valence of M is the number which represents the combining power of one element with another. For boron this is 3, aluminum is 3, silicon is 4, and titanium is 4.

If the hydrocarbon groups in $R^1$ and $R^2$ are interrupted in the backbone by nonperoxide —O—, —C(O)—S—, or —N— groups, the interrupting group is preferably an oxygen, nitrogen, or sulfur atom. The nitrogen atoms can be primary (terminal), secondary, or tertiary, but they are preferably tertiary atoms. Furthermore, if the backbone does contain oxygen, nitrogen, or sulfur atoms, it is preferably interrupted by about 1–9 of these atoms.

In preferred materials, x=y (most preferably x=3), and each $R^1$ is independently selected from the group consisting of a $C_1$–$C_{20}$ alkyl, a $C_3$–$C_{18}$ cycloalkyl, a $C_6$–$C_{18}$ aryl, and a $C_1$–$C_{18}$ acyl. More preferably, each $R^1$ is independently selected from the group consisting of a $C_1$–$C_8$ alkyl, a $C_5$–$C_8$ cycloalkyl, a $C_6$–$C_{10}$ aryl, and a $C_1$–$C_8$ acyl. Most preferably, each $R^1$ is a $C_1$–$C_3$ alkyl.

In preferred materials, each $R^2$ is independently selected from the group consisting of hydrogen, a $C_1$–$C_{20}$ alkyl, a $C_3$–$C_{18}$ cycloalkyl, a $C_6$–$C_{18}$ aryl, and a $C_2$–$C_{18}$ alkenyl. More preferably, each $R^2$ is independently selected from the group consisting of hydrogen, a $C_1$–$C_{10}$ alkyl, a $C_5$–$C_8$ cycloalkyl, a $C_6$–$C_{10}$ aryl, and a $C_2$–$C_{10}$ alkenyl. Most preferably, each $R^2$ is independently selected from the group consisting of hydrogen, a $C_1$–$C_6$ alkyl, a $C_5$–$C_6$ cycloalkyl, a $C_6$ aryl, and a $C_2$ alkenyl. Of these groups, $R^2$ preferably selected from the group consisting of hydrogen, methyl, ethyl, phenyl, and vinyl.

A single organometallic solvent according to Formula I can be used in the resin composition of the present invention. Alternatively, a mixture of several different materials according to Formula I can be used in the resin composition. Furthermore, dimeric, trimeric, and tetrameric complexes, etc., of compounds of Formula I are useful in the resin compositions of the present invention. The liquid products of partial hydrolysis and condensation of the organometallic compounds of Formula I, for example polydiethoxysiloxane, may also be utilized. Such resulting condensation polymers could be linear or branched.

In general, upon exposure to water the organometallic compounds will hydrolyze relatively rapidly. The resulting hydrolyzed materials (for example silanols in the case of M being Si) can react with other hydrolyzed molecules (and in some instances with molecules of nonhydrolyzed material) to form extended M—O—M systems (for example, silicone polymers). Such a reaction is sometimes referred to as a "condensation," because it concerns the expulsion of water or similar molecules (for example, simple alcohols). As used herein the term "condensation" is not meant to suggest any particular path of hydrolysis and follow-up reaction.

A variety of organometallic liquids according to Formula I are commercially available. These include, but are not limited to, trimethyl borate, triethyl borate, triisopropyl borate, tri-n-butyl borate, aluminum tri-sec-butoxide, diethylaluminum ethoxide, tetramethoxysilane, tetraethoxysilane, tetra-i-propoxysilane, tetraacetoxysilane, tetraphenoxysilane, tetra (2-(2-methoxyethoxy) ethoxy) silane, tetraacetoxysilane, triethoxysilane, ethyl triethoxysilane, vinyl triethoxysilane, dimethyldiethoxysilane, trimethylsilylphenoxide, diphenyldimethoxysilane, isopropenoxy trimethylsilane, methyl tri(butanone oximino) silane, titanium (IV) isopropoxide, titanium (IV) propoxide, and titanium (IV) 2-ethylhexoxide. The liquid products of partial hydrolysis of organometallic compounds, for example polydiethoxysilane, may be utilized as well.

Preferred organometallic liquids suitable for use in the resin compositions of the present invention include the silanes, borates, and titanates having 1–4 $C_1$–$C_3$ alkoxy groups (—$OR^1$ groups in Formula I). These include trimethyl borate, triethyl borate, triisopropyl borate, tetramethoxysilane, tetraethoxysilane, tetra-i-propoxysilane, triethoxysilane, vinyl triethoxysilane, and titanium (IV) isopropoxide. These are preferred at least because of availability and ease of which they undergo hydrolysis.

A more preferred group of organometallic liquids include silane compounds having 1–4 methoxy, ethoxy, or propoxy groups. These include tetramethoxysilane, tetraethoxysilane, tetra-i-propoxysilane, triethoxysilane, and vinyl triethoxysilane. The most preferred organometallic liquid is tetraethoxysilane (TEOS). TEOS has a relatively low toxicity (oral-rat LD50=6270 mg/kg), high boiling point (169° C.), and high flash point (46° C.). It has a relatively innocuous hydrolysis product (ethanol), and has a high yet controllable rate of hydrolysis. For example, it solidifies within minutes upon contact with water in the presence of a catalyst. TEOS is also readily available from numerous sources, e.g., Akzo Chemicals (Chicago, Ill.), at a low cost.

The Organic Polymer

The term organic polymer is meant to include polymers whose backbones are comprised of carbon atoms, as well as those polymers whose backbones are not comprised of carbon but contain organic groups attached in a side chain fashion, e.g., polydimethyl siloxane. The organic polymers of the present invention provide certain preferred characteristics in the cured composition relating to toughness, strength, and good physical integrity. They have a number average molecular weight of at least about 400. Preferably, the organic polymers have a number average molecular weight of about 1,000–1,000,000, and more preferably about 4,000–30,000. The polydispersity (ratio of number average to weight average molecular weight) of the organic polymers is preferably about 1–3.

Suitable organic polymers are stably dispersible, and preferably soluble, within the organometallic liquids described above. As used herein, a stably dispersible organic polymer refers to one that will form a stable colloidal dispersion with an organometallic liquid for at least about two years under moisture-free, ambient conditions. As indicated above, preferred curable resin compositions according to the present invention include an appropriate organic polymer material dissolved within the liquid organometallic compound such that polymer solutions, i.e., microscopic dispersions, are formed. Preferably, the organic polymers are soluble in the organometallic compounds in an amount of at least about 30% by weight.

The organic polymer can be reactive or nonreactive. By the term "reactive" in this context, it is meant that the material may react with itself or with the organometallic liquid, during cure upon activation by water or another hydrogen-containing molecule. For example, a resin composition containing an epoxy polymer and TEOS can be cured upon crosslinking of the epoxy polymer and hydrolysis and condensation of the TEOS.

By "nonreactive" in this context, it is meant that the organic polymer does not react with itself, with water, or with the organometallic liquid during cure, but rather it remains mixed with, or suspended in, the water-reactive organometallic domain or matrix after cure. For example, a resin composition containing polystyrene and TEOS cures upon the hydrolysis and condensation of TEOS. However, the polystyrene does not chemically react.

The polymers useful in the present invention can be either addition polymers, i.e., polymers having backbones containing primarily carbon atoms, such as polystyrene and acrylic or methacrylic acid esters, or they can be condensation polymers, i.e., polymers having backbones containing primarily carbon or silicon atoms interrupted with heteroatoms, such as polyethers, polyesters, and silicones. Thus, as used herein the "organic"

polymers generally include primarily carbon atoms in the backbone, however, they can also be polymers containing other atoms, such as silicon atoms, primarily in the backbone with carbon-containing groups attached as side groups. An example of such an "organic" polymer as used herein is polydimethylsiloxane, Addition polymers are preferably utilized as the organic polymer constituent. This is generally true because addition polymers are easier to prepare in situ, i.e., directly in the organometallic liquid, than condensation polymers. Furthermore, because they are easier to make, they can be tailor made with specific properties. Thus, a greater number of addition polymers not commercially available can be made for use in the resin compositions of the present invention. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl naphthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoethyl methacrylate, 3-methacryloxypropyltris(trimethylsiloxy)silane, isobutyl methacrylate, itaconic acid, vinyl acetate, vinyl stearate, N,N-dimethylacrylamide, tert-butyl acrylamide, acrylonitrile, isobutyl vinyl ether, vinyl pyrrolidinone, vinyl azlactone, glycidyl methacrylate, 2-isocyanatoethyl methacrylate, vinyl methyl dimethoxysilane, maleic anhydride, vinyl triethoxysilane, vinyl tris(2-methoxyethoxy)silane, and 3-(trimethoxysilyl)propyl methacrylate.

In certain situations, it is desirable to use polymers bearing hydrolyzable silane functionality, i.e., alkoxy silane functionality, because the pendant silane moiety can provide a site for covalent coupling of the organic and inorganic phases. In certain other situations, it is desirable to avoid the use of polymers containing pendant hydrolyzable silane groups.

A preferred group of monomers useful in the preparation of the addition polymers of the resin compositions include butadiene, styrene, isobutyl methacrylate, maleic anhydride, vinyl triethoxysilane, 3-(trimethoxysilyl)propyl methacrylate, and mixtures thereof. A more preferred group of monomers useful in the preparation of the addition polymers of the resin compositions include, is 3-(trimethoxysilyl)propyl methacrylate, isobutyl methacrylate, vinyl triethyoxysilane, and mixtures thereof, at least because they result in a more completely cured product and/or less toxic by-products.

Also as indicated above, condensation polymers are useful as the organic polymer that is mixed with the organometallic liquid, preferably dissolved in the organometallic liquid, in resin compositions according to the present invention. In general, useful condensation polymers are those possessing, for example, backbone ester, carbonate, amide, carbamate, urea, silicone (—Si—O—Si—O) or sulfone linkages. Preferably, the condensation polymers do not include polyethers and other ether-containing organic polymers. At least in part this is because compositions incorporating such condensation polymers are not generally weather resistant. That is, for example, they may yellow. Thus, the resin compositions of the present invention that include condensation polymers preferably include nonether-containing condensation polymers. Condensation polymers possessing more than one functional group, for example, poly(ester-amide)s, are also useful. Polyesters, for example, poly(neopentyl glycol sebacate) and poly(caprolactone), and polyethers, for example, poly(propylene oxide), are preferred condensation polymers because of their good solubility and because they are relatively inexpensive.

Useful condensation polymers include those bearing hydrolyzable silane functionality, i.e., alkoxy silane groups of the formula —SiOR wherein R represents a hydrocarbon, preferably an alkyl group. These can be prepared, for example, from reaction of an alcohol-, mercaptan-, or amine-functional condensation polymer with, for example, 3-isocyanatopropyltriethoxysilane. Useful organic polymers containing hydrolyzable silane groups are those described in U.S. Pat. Nos. 4,411,262 and 4,510,622 (von Bonin et al.). These can be used to advantage in combination with the liquid organometallic compound described above. As stated above, in certain situations, however, it may also be desirable to use polymers without hydrolyzable silane functionality.

In the organic polymer component, nonreactive substituents that can be affixed to the polymer backbone include hydrogen, fluorine, and chlorine atoms, as well as alkyl, alkenyl, aryl, carboalkoxy, carbamide, alkoxy, carboxyl, nitrile, pyrrolidinone, and carboxylic acid groups. Reactive substituents that can be affixed to the polymer backbone include hydrolyzable silane, acrylate, methacrylate, epoxy, aziridine, isocyanate, anhydride and azlactone groups.

The term "organic polymer" (as used herein with respect to the polymer component of molecular weight at least 400) is meant to include within its scope copolymers, that is, polymers derived from several different monomers reacted in random or block order, for example, poly(styrene-co-butadiene), poly(acrylonitrile-co-butadiene-co-styrene), or poly(octadecyl vinyl ether-co-maleic anhydride). The term "organic polymer" in this context is further meant to include within its scope polymer blends formed from the combination of two or more dissimilar polymers, for example, an intimate mixture of poly(styrene) and poly(styrene-co-butadiene).

The choice of monomer or comonomers used to prepare either the addition or condensation polymers will affect the physical properties of the final cured product. In general, if a soft, i.e., flexible or semi-rigid, product is desired, monomers that contribute to a low glass transition temperature (Tg), e.g., −60° C. to 20° C., should be incorporated into the polymer. If, however, a harder, i.e., rigid, product is desired, monomers that contribute to a higher Tg, e.g., 20° C. to 120° C., should be incorporated into the polymer.

As stated above, the organic polymer used in the resin compositions of the present invention have a number average molecular weight of at least about 400, preferably about 1,000–1,000,000, and more preferably about 4,000–30,000. Procedures for controlling the molecular weights of polymers during their preparation are known. The molecular weights of condensation polymers can be controlled, for example, by varying the stoichiometry of the monomers chosen or by inclusion of monovalent or polyvalent monomers. The molecular weight of addition polymers can be controlled by factors such as monomer identity and concentration, solvent identity, initiator and chain transfer agent identity and concentration, and polymerization temperature.

It is to be understood that the resin compositions of the present invention can include a combination of polymers with reactive groups that could be cured by UV, heat, or water. Such dissimilar polymers could be cured simultaneously or in a staged manner in which there could be an initial cure step followed by a subsequent cure step.

Preparation of the Resin Compositions

The resin compositions of the present invention can be prepared by various methods. This can include: (a) dissolving or dispersing a preformed polymer directly in an organometallic liquid; (b) adding an organometallic liquid to an existing solution of a polymer in an organic solvent and subsequently removing the organic solvent; and (c) synthesizing a polymer in the organometallic liquid itself.

In many instances, it will be useful to directly synthesize the organic polymer within the organometallic liquid. This will be preferred, for example, when the desired organic polymer is not commercially available or when the desired organic polymer (if preformed) is difficult to dissolve within the organometallic liquid. The methods of direct synthesis of the organic polymer are analogous to the methods used in polymer formation in the absence of the organometallic compound. These methods are known to one of skill in the art.

The method of direct synthesis of the organic polymer (i.e., synthesis within the organometallic liquid) is particularly attractive when the organic polymer is an addition polymer. Addition polymerization may be conducted using standard free radical, cationic, anionic or group transfer polymerization techniques. Useful monomers include, but are not limited to, acrylates, methacrylates, acrylamides, vinyl esters, vinyl aromatics, vinyl ethers, and vinyl heterocycles. Specific examples of useful monomers include ethyl acrylate, isobutyl methacrylate, N,N-dimethylacrylamide, vinyl acetate, styrene, isobutyl vinyl ether, and vinyl carbazole.

The polymerization may be initiated thermally, photochemically or by other means known in the art. Useful polymerization initiators include, but are not limited to, azo- and peroxide-functional compounds, substituted acetophenones and benzophenones, and iodonium salts. Specific examples of useful initiators include azobis(isobutyronitrile), tert-butylperoxybenzoate, OO-tert-butyl—O—(2-ethylhexyl)monoperoxycarbonate, benzoin ethyl ether, 2,2-dimethoxy-2-phenylacetophenone, 4,4'-bis(dimethylamino)benzophenone and diphenyliodonium chloride. The monomers and initiators in this method can independently be added continuously or in a batchwise mode to the organometallic liquid. A typical temperature range for synthesis of a polymer from at least one type of monomer dissolved in an organometallic compound is about 70°–140° C.

Direct formation of a polymer composition in an organometallic liquid can be performed by contacting a polymer with an organometallic liquid, wherein the composition of the mixture is from 1–99% by weight of an organometallic liquid and from 99–1% by weight of a polymer, preferably from 10–70% organometallic liquid and from 90–30% polymer. The mixture may be optionally agitated and/or warmed to facilitate dispersion, preferably solution, formation. Mechanical stirring of the mixture is preferred and heating of the mixture at temperatures up to and including the boiling point of the organometallic liquid is preferred. Temperatures above the boiling point of the liquid, attainable for example in a sealed reactor, may be useful. Generally, and preferably, the mixture of organic polymer and liquid organometallic compound is heated at a temperature of about 80°–160° C.

Solution formation by way of solvent exchange is useful and is preferred when working with polymers which are not readily soluble in organometallic liquids. This method comprises the steps of: (a) synthesizing an organic polymer or dissolving a preformed organic polymer in an organic solvent (preferably a common organic solvent possessing a boiling point lower than that of the organometallic liquid to be used as the ultimate polymer solvent, for example acetone, methyl ethyl ketone, toluene, 1,2-dichloroethane, tetrahydrofuran, or ethyl acetate); (b) diluting the polymer solution with the desired organometallic liquid; and, (c) removing the organic solvent, for example by warming the polymer solution and allowing the organic solvent to distill; or, more preferably, by conducting the solvent distillation at a reduced pressure (with or without heating). Most preferably, the reaction mixture is heated at a temperature of about 80°–120° C. and the solvent is removed under vacuum.

Compositions according to the present invention should be formulated to preferred viscosities, for application to substrates and retention thereon. That is, they should be of a viscosity that can be readily used to coat or impregnate a sheet of substrate material and which will stay in place as the sheet of material is wrapped around a limb or other structure, prior to cure. The preferred resin compositions are fluids having viscosities of about 5,000–500,000 cps, preferably about 10,000–100,000 cps, at room temperature (20°–30° C.). This can be achieved by controlling the molecular weight of the polymer, by adjusting the solids content (level of polymer and adjuvants) of the resin composition, and/or by adjusting the content of thixotropic fillers.

Adjuvants

Preferred compositions according to the present invention can include a variety of adjuvants therein. It is foreseen that adjuvants such as: surfactants, slip agents or tack reducing agents, toughening agents, fillers, pigments (or dyes), fragrances, and/or catalysts will most typically be used.

Surfactants

The curable resin compositions may optionally include a surfactant. The incorporation of a surfactant may be desirable to improve flow of the resin composition into the fiber bundles of the fabric substrate, to reduce entrainment of air bubbles in the resin composition during resin preparation and coating, and to increase wetting during water activation of the resin-coated fabric. Useful flow aids include surfactants such as Fluorad® fluorochemical surfactants FC-430, FC-431, and FC-170C available from 3M Co. (St. Paul, Minn.), Masil® SF polydimethylsiloxane fluids available from Mazer Chemicals Inc. (Gurnee, Ill.), Silwet L-720 modified polydimethylsiloxane available from Union Carbide (Danbury, Conn.), and Perenol S silicone adducts available from Henkel Corporation (Teaneck, N.J.). Useful air release agents include materials such as Dehydran ARA 7219, a mixture of organic materials available from Henkel Corp., and Airout, a modified silicone available from Isochem Resin Co., Lincoln, R.I. Useful wetting agents include surfactants such as Findet A-100-UH, complex phosphate esters available from Finetex, Inc. Spencer, N.C., Gemtex, a dioctyl sulfosuccinate available from Finetex Inc., Igepal CO-720, an ethoxylated alkylphenol available from GAF Corp. (NY, N.Y.), Macol ®, a fatty alcohol ether available from Mazer Chemicals, (Gurnee, Ill.), Pluronic, various block copolymers of polyoxypropylene and polyoxyethylene available from BASF Wyandotte Corp (Parsippany, N.J.), and Carbowax ®, a polyethylene glycol available from Union Carbide Corp. (Charleston, W. Va.). Generally, if surfactant is used at all, what is required is that an amount of the surfactant(s) be used which is necessary to achieve the desired effect. Typically, the surfactants will be used at levels of 0.1-1.0% by weight and preferably 0.2-0.5% by weight.

Slip Agents or Tack Reducing Agents

The useful curable resin compositions of the present invention may also include a slip agent or tack reducing agent. Such agents are disclosed in U.S. Pat. Nos. 4,774,937 and 4,667,661, which are incorporated herein by reference. Preferred agents include, but are not limited to, poly(ethylene oxide), butylene oxide-ethylene oxide block copolymers, propylene oxide-ethylene oxide block copolymers, and polydialkylsiloxanes. Generally, if a slip agent or tack reducing agent is used at all, what is required is that an amount of the agent(s) be used to achieve the desired effect of reduced tack prior to and/or during cure, such that the resin does not stick to the gloves of the medical practitioner. Typically, an amount is used such that the resin composition has a coefficient of friction of less than about 2 and preferably less than about 1.2. To achieve this result, the amount of slip agent(s) or tack reducing agent(s) used is typically about 1-10 wt-%, preferably 2-4 wt-% based on the total weight of the resin composition.

Toughening Agents

Toughening agents may also be included in the curable resin compositions of the present invention to increase the strength of the cured material. Such agents can comprise carboxy, amine, methacrylate, and vinyl terminated butadiene-acrylonitrile polymers available from BF Goodrich (Cleveland, Ohio). Thermoplastics such as styrene-butadiene copolymers available from Shell Chemical Co. (Houston, Tex.), polyurethanes, and polytetrafluoroethylene can also be useful as toughening agents. In addition, core/shell polymers such as those comprising a rubbery phase and thermoplastic phase such as graft polymers having a polydiene rubbery core, such as a styrene-butadiene block copolymer, and a poly(meth)acrylate shell available for example as BTA IIIF from Rohm & Haas (Philadelphia, Pa.) may be useful as toughening agents in the curable resins of the present invention. Furthermore, plasticizers such as dioctyl phthalate and butyl benzyl phthalate may be used to soften, reduce brittleness and thereby toughen the cured material. Generally, if a toughening agent is used at all, what is required is that an amount of the agent be used to achieve the desired effect. Typically, up to about 50 wt-%, preferably up to about 10 wt-%, is used in the resin compositions of the present invention.

Fillers

Fillers may also be used in the curable resin compositions to increase strength of the cast obtained, reduce cost, and adjust viscosity, thixotropy or overall fluid flow properties of the curable resin. Fillers can also be used to modify appearance and handling characteristics of the coated sheet material. Useful fillers include, but are not limited to, aluminum oxides, calcium metasilicate, titanium dioxide, fumed silica, amorphous silica, ground glass, glass fibers, glass bubbles, glass microspheres or mixtures of these materials. Additional fillers may include particles of polypropylene, polyethylene, or polytetrafluoroethylene. In general, if a filler is used at all, what is required is that enough filler be used to achieve the desired effect. Typically, up to about 50 wt-%, preferably about 5-20 wt-%, and more preferably about 5-15 wt-%, is used in the resin compositions of the present invention. Calcium metasilicate fillers are particularly preferred in the case of rigid orthopedic casting tape materials and are discussed in commonly assigned, copending U.S. application Docket No. 49125USA3A filed on even date herewith, incorporated herein by reference.

Colorants

The color of the curable resin composition of the present invention may be effected by colorants, such as inorganic pigments, organic pigments, and dyes. Suitable colorants include those disclosed in U.S. Pat. Nos. 5,005,566 and 5,052,380. Hydroxyfunctional colorants may be chemically bound into the curable resin composition by condensation with —SiOH groups on the polymer or by first being functionalized with a vinyl group through reaction with isocyanatoethyl methacrylate or vinyldimethylazlactone, and then being copolymerized with the above-described monomers in the preparation of the resin of the present invention. In general, if pigments or dyes are used at all, what is required is a sufficient amount of the pigments or dyes to achieve the desired effect. Typically, up to about 5 wt-% can be used in the resin compositions of the present invention.

A typical pigment used is $TiO_2$ to impart a white color to the cast. This component can also be used as a filler. Thus, for materials that can be used as both pigment and filler, such as $TiO_2$, up to about 15 wt-% can be used.

Fragrance

It may be desirable to include a fragrance in the resin to make the experience of having a cast put on more pleasant for the patient and to mask unpleasant odors that may arise after prolonged wear from body odor and microorganisms. Examples of fragrances which may be included are lemon, peach, strawberry, apricot, fruit punch, cinnamon, juniperberry, baby powder, sandalwood, and frankincense. Such fragrance additives are available from Stanley S. Schoenmann, Inc. (Clark, N.J.), Berje (Bloomfield, N.J.) and Atlanta Fragrance, Inc. (Marietta, Ga.). In general, if a fragrance is used at all, what is required is sufficient amount of fragrance to achieve the desired effect. Typically, up to about 1.0 wt-%, preferably up to about 0.5 wt-%, is used in the resin compositions of the present invention.

Catalysts

The resins useful in the present invention may be cured in the presence of a catalyst to increase the rate of hydrolysis and condensation of the organometallic liquid and polymerization of the organic polymeric network. Either acidic or basic catalysts may be useful. Preferred catalysts are acid catalysts, whether an organic or an inorganic acid catalyst. Of the acid catalysts, the preferred ones are those having a pKa of less than about 3.0. The most preferred acid catalysts are those that lower the pH of the resin composition to below 3.

Acid catalysts include, but are not limited to, alkylsulfonic acids such as ethanesulfonic acid, arylsulfonic acids such as benzenesulfonic acid, poly(perfluoroalkylsulfonyl)alkanes such as bis(trifluoromethylsulfonyl)methane, polyhaloalkanesulfonic acids such as trifluoromethanesulfonic acid, aliphatic carboxylic acids such as trifluoroacetic acid and acetic acid, phosphate ester compounds such as diethylphosphate and dibutylphosphate, and strong inorganic acids such as hydrochloric acid, sulfuric acid, and nitric acid. A preferred acid catalyst is selected from the group consisting of an alkanesulfonic acid, a perfluorocarboxylic acid, a bis(perfluoroalkylsulfonyl)methane, a dialkyl phosphate, and mixtures thereof. A more preferred acid catalyst is selected from the group consisting of ethanesulfonic acid, trifluoroacetic acid, bis(trifluoromethylsulfonyl)methane, diethylphosphate, and mixtures thereof. A preferred acid catalyst imparts a short cure time to the resin composition at room temperature.

Compounds that generate useful acids on contact with water may also be useful catalysts and include, but are not limited to, boron trifluoride etherate, acetyl chloride, p-toluenesulfonyl chloride, trifluroacetic anhydride, thionyl chloride, and tetrachlorosilane.

Base catalysts useful in the practice of the present invention include, but are not limited to, dimorpholino diethyl ether, 1,1,3,3-tetramethylguanidine, 1,8-diazabicyclo[5.4.0]undec-7-ene, 1,4-diazabicyclo[2.2.2]octane, 4-dimethylaminopyridine, triethylamine, dibutyltin oxide, calcium hydroxide, dibutyltin diacetate, and ammonium carbonate.

A strong acid catalyst or a strong base catalyst is preferred when a fast cure is desired. A relatively weak acid catalyst or base catalyst is preferred to promote slow cures. In general, if a catalyst is used at all, all that is required is sufficient catalyst to achieve the desired effect, i.e., an effective amount. In general, at least about 0.5 wt-%, preferably about 1.5-3.0 wt-%, is used in the resin compositions of the present invention.

Preparation of the Uncured Casting Material

The uncured casting material comprises a substrate or scrim impregnated with the uncured resin. In general, it is desired that the casting tape be constructed from a fabric or substrate which is relatively stretchable and flexible; i.e., which has a lengthwise extensibility of about 15-70%, preferably about 20-50%, once coated with the uncured resin. This will facilitate fitting the casting tape around contoured portions of the body, such as the heel, knee or elbow. Furthermore, it is desired that the casting tape be constructed from a porous or mesh fabric, i.e., a fabric having apertures of sufficient size to enable water to permeate the roll of casting tape during water activation and cause the resin to set after application to a body part or other structure. In addition, a porous fabric is desired to allow air and moisture vapor to move through the material after cure, thereby promoting patient comfort and avoiding skin breakdown caused by excessive moisture build-up under the cured material. Suitable aperture sizes are about 0.3-16 mm$^2$, preferably about 1.2-9 mm$^2$. Where an impermeable occlusive wrap is desired, a nonapertured fabric may be desired. In this case, water may be added to the coated material as it is applied for optimum cure speed.

Suitable substrates include knit, woven, and nonwoven fabrics as well as foams and other porous materials made of natural or synthetic fibers. Examples of preferred fiber materials from which flexible casting tapes can be formed include, but are not limited to, fiberglass, nylon, polyolefins, and polyesters. Other usable materials include knits, wovens, and nonwovens containing elastic yarns or fibers of natural rubber or polyurethane. The backings may be dyed or pigmented in a solid or patterned manner, as discussed in commonly assigned, copending U.S. application Ser. No. 751,725 filed Aug. 29, 1991, incorporated herein by reference.

A more preferred fiber material from which stretchable casting tapes can be formed is fiberglass. Fiberglass is relatively strong and inexpensive. When used with the water-curable resin of the present invention, the combination cures to a very hard, lightweight, strong, weight-bearing cast. While fiberglass yarns themselves are relatively inelastic, they can be knitted into a highly extensible knit fabric or substrate. Fiberglass woven or knitted substrates suitable for use in casting tapes according to the present invention include those used in the knitted substrate of Scotchcast ® Plus casting tape, which tape is available from 3M Company (St. Paul, Minn.). Another preferred fabric is disclosed in Ersfeld et al., U.S. Pat. No. 4,841,958, wherein an apertured nonwoven fabric is described.

The substrate can be coated or impregnated with the resin composition by any of a variety of means well known in the art, depending on the viscosity of the resin composition. For example, low viscosity compositions can be sprayed onto a substrate. A resin composition of high viscosity can be applied to a substrate as a putty. A resin composition of moderate viscosity can be applied to a substrate by brush, knife coating, curtain coating or with a roll coater.

As a typical example, the resin composition is applied to a substrate by spreading the resin onto the surface of the substrate by knife coating or other similar method and allowing the resin to level and soak into the substrate. Some manipulation such as pressuring or kneading of the resin into the substrate may sometimes be desirable.

The amount of the resin composition applied to the substrate can vary considerably depending on the actual viscosity of the composition and the end use of the material. Typically, the fabric is impregnated with the water-curable multicomponent resin composition in an amount of about 0.1-0.3 g of resin per square inch of the material forming the fabric. Preferably, fiberglass fabric is used and impregnated with the resin composition in an amount of about 40-50% by weight of the impregnated casting material.

A variety of conventional techniques can be utilized to store the uncured resin-coated substrate, prior to use to form a cast. Typically a roll of the coated substrate of appropriate length will be prepared, and the roll will be packaged within a substantially water-impermeable, air-tight container such as a metal-lined plastic container. When stored in this manner, uncured casting materials according to the present invention are generally shelf stable for an indefinite period of time, typically at least one year under a wide range of conditions, such as temperatures of about 0°-40° C., and preferably under ambient conditions, i.e., at temperatures of 20°-30° C. As used herein, "shelf stable" or "stable" means that the organic polymer and the liquid organometallic compound do not phase separate, i.e., they do not separate out of a colloidal dispersion or solution into generally separate and individual phases, nor do they react substantially with each other or with themselves during storage at a temperature of about 0°-40° C. Furthermore, when kept from moisture, the compositions remain flowable, flexible, pliable, and capable of adhering to the desired substrate.

Preparation of a Cured Cast

Cure of the resin-coated sheet of the present invention is accomplished by contacting the curable resin composition with water. In the presence of water the organometallic solvent of the resin composition hydrolyzes and condenses, preferably forming discreet crosslinked metal oxide domains in association with the organic polymer matrix used therein. When the polymer contains alkoxysilane groups these too may hydrolyze and condense in the presence of water, preferably causing the polymer to crosslink and bond with the metal oxide domains.

The resin-coated sheet may be contacted with water by such means as absorption of moisture from the atmosphere, spraying its surface with water, and dipping the resin-coated sheet in water. The rate of cure of the resin-coated sheet can be increased by elevating the water temperature, and thereby increasing the reaction rate. In addition, by assuring maximum water contact with all surfaces, the amount of water diffusing into the resin can be increased, resulting in a faster and more complete cure. The use of surfactants and other hydrophilic additives which promote the absorption or diffusion of water into the resin composition can produce a similar effect.

The resin composition can be cured upon exposure to water under a variety of conditions of temperature and pressure. For example, it can cure at a temperature of about 10°-100° C., and preferably about 20°-50° C. Advantageously, however, extreme temperatures are not required. That is, the resin composition of the present invention advantageously can cure under ambient conditions, i.e., about 20°-30° C. and about 1 atmosphere.

Cure time of the resin-coated sheet can also be decreased by elevating the catalyst concentration, using a more reactive organometallic solvent, and increasing the number of hydrolyzable silane groups or other crosslinkable groups in the polymer. That is, the rate of hydrolysis of the organometallic solvent is dependent upon the identity of the metal present and the nature of the groups attached to the metal. For example, titanates and borates hydrolyze more quickly than the analogous silicates. For a given metal, organometallic solvents based on alcohols of lower steric hindrance will, in general, hydrolyze more rapidly than those with greater steric hindrance.

Orthopedic casting materials, involving the water-curable resin compositions of the present invention are applied to humans or other animals in the same fashion as other known orthopedic casting materials. First, the body part to be immobilized is preferably covered with a conventional cast padding and/or stockinet for protection. Generally, this is a protective sleeve of an air-permeable fabric such that air may pass through the sleeve and the cast to the surface of the skin. Preferably, this sleeve does not appreciably absorb water and permits the escape of perspiration. An example of such a substrate is a knitted or woven crystalline polypropylene material.

Next, the curable resin is activated, for example, by dipping the orthopedic casting material in water. Excess water is then squeezed out of the orthopedic casting material, and the material is wrapped or otherwise positioned around the body part so as to properly conform thereto. Preferably, the material is then molded and smoothed to form the best fit possible and to properly secure the body part in the desired position. Although often not necessary, if desired the orthopedic casting material may be held in place during cure by wrapping an elastic bandage or other securing means around the curing orthopedic casting material. When curing is complete, the body part is properly immobilized within the formed orthopedic cast or splint.

The orthopedic casting material has a working time sufficient to allow the bandage to be positioned, a set time sufficient for the cast to take the shape of the body part, and a cure time sufficient for the cast to become weight-bearing. The working time is about 1-3 minutes, preferably about 1.5-3 minutes. The set time is about 3-15 minutes, preferably 3-5 minutes. The cure time is about 0.5-24 hours, preferably about 0.5-7 hours.

Other Applications

In addition to orthopedic support materials, the water-curable resin-coated substrates, e.g., sheets, of the present invention can be used for any application where wrapping an object is desirable. For example, such coated substrates can be used to wrap pipes for joining, reinforcement, leak stoppage, protection from abrasion or other abuse, or prevention of escape of insulation fibers such as fiberglass or asbestos. In addition, duct work or other structures that can be wrapped could benefit in a similar manner. Furthermore, such coated substrates can also be used to repair broken or damaged tools such as hoe handles, shovel handles, rake handles, and the like. Sporting equipment can also be reinforced or repaired by wrapping with the present coated substrates. For example, softball and baseball bats and hockey sticks can be wrapped with this material. The coated substrates of the present invention can also be used for patching or bridging gaps to provide a surface for filling and repairs.

Preferred Embodiments

| Generic Composition | |
|---|---|
| Polymer (Unreactive or Reactive) | 50-95% |
| Reactive Polymer Composition: | |
| Peroxide catalyst | 1-5% |
| Aryl or lower ($C_1$-$C_8$) alkyl methacrylate | 50-90% |
| Alkoxysilylalkyl methacrylate | 0-30% |
| Vinyl alkoxysilane | 0-30% |
| Organometallic Compound | 5-50% |
| Water Cure Catalyst | 1-5% |
| Slip Agent | 2-5% |
| Fragrance Additive | 0.1-1% |

All percentages and "parts" used herein are based on the total weight of the resin composition, unless otherwise stated.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention. All starting materials used in the following examples are available from Aldrich Chemical Co. (Milwaukee, Wis.) unless otherwise specified.

EXAMPLES

Example 1

A polymer solution in tetraethylorthosilicate (TEOS) was prepared by initially dissolving 60 grams of nominal 45,000 molecular weight polystyrene in 90 grams of TEOS at about 120° C. A 40 gram sample of nominal 280,000 molecular weight polystyrene was added and the mixture was heated at reflux in a flask equipped with a mechanical stirrer, condenser, inlet port, and temperature controlled heating mantle. The solution was cooled to room temperature. A polyethylene oxide-4-nonylphenol monoether surfactant (1.45 gram), available under the tradename Igepal ® CO-720, and acetyl chloride catalyst (0.9 gram) were mixed in.

In a low humidity environment (less than 7% RH), the resulting polyester/TEOS resin (46.8% TEOS) was hand coated onto a 3 inch (7.6 cm) wide by 40 inch (102 cm) long strip of knit fiberglass fabric, described in the example of U.S. Pat. No. 4,609,578, by spreading the resin onto the fabric and then kneading the resin in by hand to more uniformly distribute the resin. The resin content was 42.5% (weight percent) in the coated fabric which was then rolled onto a plastic core and sealed in a foil lined pouch.

The above sheet material was water activated by removing the rolled material from the pouch, submerging the roll in 23° C. water with squeezing for about 30 seconds. Excess water was squeezed out and then the sheet was wrapped in 6 layers onto a polyester stockinet-covered, 2 inch (5.1 cm) diameter mandrel. The material in the form of a six-layer cylinder was set to the shape of the mandrel within about 15 minutes. After 4 days at about 22° C. and about 50% relative humidity, the strength of the cured cylinder was measured under compression in an Instron model 1122 tensile tester apparatus with a 100 pound (453.6 kg) load cell, so that the overlap seam was not contacted by the penetrating bar (described below) of the compression test fixture. The compression test fixture had an upper and a lower base. The lower base was attached to the Instron tensile tester and the upper base was attached to the load cell. The lower base was equipped with two rectangular metal bars dimensioned to approximately 1.90 cm wide, 1.27 cm thick, and 15.2 cm long, and the bars were attached to the metal base about 3.81 cm apart. The cured ring was in turn placed on these bars and rested against the inside, rounded edges (having a radius of about 0.381 cm). The penetrating bar, approximately 0.635 cm wide, 1.91 cm thick, and 15.2 cm long, was mounted to the upper base with a half round edge (having a radius of 0.381 cm) centered above and aligned parallel to the two bars on the lower base. The penetrating bar was lowered against the cured ring, and the maximum load sustained by the ring before failure was recorded.

Following the above procedure, the average ring strength of the ring of this Example 1 was determined to about 3.1 kg/cm of cylinder length when using a cylinder 7.6 cm long and 5.1 cm in diameter (I.D.). This example evidences the significant ring strength which can be achieved using a polymer solution of the present invention.

Example 2

A polymer solution in TEOS was prepared by placing 120 parts of TEOS in a reaction vessel equipped with mechanical stirring, nitrogen purge, addition apparatus, thermometer, and exterior heating. A mixture comprised of 8.4 parts t-butyl perbenzoate (a polymerization initiator, supplied by Atochem North America, Inc. Buffalo, N.Y.), 196.0 parts isobutyl methacrylate (supplied by Rohm and Haas, Philadelphia, Pa.), and 84.0 parts 3-(trimethoxysilyl)propyl methacrylate (supplied by Union Carbide, Sisterville, W. Va.) was purged with nitrogen and slowly added with mixing to the TEOS held at 140° C. over a 1.75 hour period. After addition was complete, the solution was held at this temperature with stirring for an additional 1.5 hours. The solution was then cooled to 120° C. and 0.8 parts t-butyl perbenzoate was added. This solution was held at 120° C. for 1 hour. After cooling, the above resin (400 parts) was combined with 6 parts of bis(trifluoromethylsulfonyl)methane (DS) (supplied by 3M Company, St. Paul, Minn.) as the catalyst, using sufficient heat to dissolve the DS.

The resulting poly(isobutyl methacrylate-co-methacryloxypropyltrimethoxysilane)/TEOS resin (28.9% TEOS) was coated onto a 3.66 meter length of the knit fiberglass fabric used in Example 1 at a resin content of 45% as described in Example 1.

A short arm cast was prepared on a human arm using the above material by water activating the material as in Example 1 and wrapping the material onto the human arm. The arm was covered first with one layer of polyester stockinet and two thicknesses of polyester cast padding. The cast was set to the shape of the arm in about 4 minutes and was stiff in about 11 minutes. The cast was removed by cutting it with a cast saw after 20 minutes. This experiment showed that an orthopedic cast, which sets in the shape of a body and provides support within minutes, can be made with this material. Furthermore, conventional means of removal can be used.

Example 3

A resin solution prepared as described in Example 2 was machine coated onto knit fiberglass fabric (of the type described in Example 1) at 43.2% (weight percent) resin solution. Six layer test rings prepared as described in Example 1 from 3.66 meter lengths of coated fabric were tested for ring strength as described in Example 1 immediately after soaking in 45° C. water for 30 minutes. A ring strength of 29.7 pounds per inch (5.3 kilograms per cm) was obtained. When six-layer test rings prepared the same way were tested without soaking, i.e., dry, the ring strength was found to be 38.3 pounds per inch (6.9 kg/cm). Only 23% of the dry ring strength was lost from soaking in 45° C. water. This demonstrates that the cured product has superior strength in the presence of warm water, as could be encountered in a hot shower.

Example 4

A polymer solution in TEOS was prepared as in Example 2 above except that the solution was heated at 110° C. for an additional 19 hours. The resulting resin was coated onto a 3.05 meter length of knit fiberglass fabric as in Example 3 at a weight of 42.5% resin. Two 1.09 meter lengths of coated fabric were taken from the sheet, rolled onto 1.9 cm diameter plastic cores, and sealed in foil lined pouches. Two six layer test rings were prepared from these rolls as in Example 1, and after curing were found to have ring strengths of 40.7 pounds/inch (7.27 kg/cm) and 41 pounds/inch (7.33 kg/cm), respectively, using the test method in Example 1. This example shows that after curing a strong composite is achieved.

Example 5

Using the general method described in Example 2, various copolymers of alkyl methacrylates and 3-(trimethoxysilyl)propyl methacrylate (MPTMS) were prepared in various levels of TEOS with 1.5% (weight percent) bis(trifluoromethylsulfonyl)methane as the catalyst. These various poly(alkyl methacrylate-co-methacryloxypropyltrimethoxysilane)/TEOS resins, i.e., methacrylate/MPTMS copolymers in TEES, were coated on the preferred knit fiberglass fabric used in Example 1 and rolled onto plastic cores and stored in foil lined pouches as in Example 1. The rolls were then evaluated for ring strengths, with the ring strengths being measured as described in Example 1. Set times were measured by lifting a one layer section of activated material 2.54 cm from its end and across its full width with the edge of a spatula. When the material did not sag when lifted it was considered set and the length of time elapsed from water contact to set was recorded. The results are listed in Table 1. These results indicate that a range of strengths and set times can be obtained by varying the constituents of the multicomponent resin and the amounts and ratios of constituents.

TABLE 1

Set times and ring strengths of methacrylate/(MPTMS) copolymers in tetraethylorthosilicate on fiberglass fabric.

| Methacrylate | Methacrylate: Silane | % Polymer In TEOS | Set Time (min) | Ring Strength (lbs/in) | (kg/cm) |
|---|---|---|---|---|---|
| n-butyl | 90:10 | 70 | 13 | 9.5 | 1.7 |
| n-butyl | 70:30 | 70 | 3 | 32 | 5.7 |
| n-butyl | 70:30 | 75 | 2.5 | 34 | 6.1 |
| n-butyl | 70:30 | 80 | 2 | 34 | 6.1 |
| isobutyl | 95:5 | 70 | 9 | 27 | 4.8 |
| isobutyl | 90:10 | 70 | 10 | 29 | 5.2 |
| isobutyl | 80:20 | 70 | 8 | 41 | 7.3 |
| isobutyl | 70:30 | 50 | 5 | 23 | 4.1 |
| isobutyl | 70:30 | 60 | 4 | 35 | 6.3 |
| isobutyl | 70:30 | 70 | 3 | 40 | 7.1 |
| isobutyl | 70:30 | 75 | 2–2.5 | 42 | 7.5 |
| isobutyl | 70:30 | 80 | 2 | 43 | 7.7 |
| isobutyl | 60:40 | 70 | 1.75 | 31 | 5.5 |
| cyclohexyl | 90:10 | 55 | 9 | 14 | 2.5 |
| t-butyl | 90:10 | 60 | 5 | 11 | 2.0 |
| Scotchcast ® Plus | N/A | N/A | 2.5–3.5 | 50 | 8.9 |

Examples 6 & 7

A nitrogen purged solution containing isobutyl methacrylate (199.5 grams), 3-(trimethoxysilyl)propyl methacrylate (10.5 grams), and tert-butyl peroxybenzoate (6.90 grams) was added dropwise over a 2.3 hour period to nitrogen purged metal alkoxide (90.0 grams) at 140° C. with stirring. The clear, colorless solution was held at 140° C. for one additional hour and then was cooled to 120° C. A second charge of peroxide (0.6 grams) was added, and the solution was stirred and held at 120° C. for one hour and then allowed to cool to room temperature.

| Example | Metal Alkoxide |
|---|---|
| 6 | Tetraisopropyl titanate |
| 7 | Triisopropyl borate |

The resin solution (78 grams) of Example 7 was combined with the catalyst bis(trifluoromethylsulfonyl)methane (DS) (1.2 grams) with sufficient heat and mixing to uniformly dissolve the DS. In Example 6, when the metal alkoxide was tetraisopropyl titanate, no DS was added.

The resulting catalyzed resin solutions were coated onto 3.66 meter lengths of knit fiberglass fabric of the type in Example 1. Coated fabrics were made into 6 layer test rings as in Example 1 by dipping the roll of coated fabric in 22° C. water for a few seconds and immediately wrapping the coated fabric onto the mandrels.

The set time of the coated fabrics were determined on the remaining material as described in Example 5. The ring strengths were determined as described in Example 1 after the six-layer rings had cured over a 15 day period.

| Example | Set Time (min) | Ring Strength (lbs/in) | kg/cm |
|---|---|---|---|
| 6 | ~1 | 11 | 2.0 |
| 7 | ~2.5 | 21 | 3.8 |

Example 8

A polymer solution containing vinyltriethoxysilane (A-151, Union Carbide) was prepared by placing 80 parts TEOS and 64 parts A-151 in a reaction vessel equipped with a mechanical stirrer, nitrogen purge, addition means, temperature monitoring, and heating means. A mixture comprised of 9.6 parts OO-t-butyl-O-(2-ethylhexyl) monoperoxycarbonate (TBEC, supplied by Atochem North America, Inc.), 224 parts isobutyl methacrylate (supplied by Rohm & Haas, Philadelphia, Pa.), and 32 parts 3-(trimethoxysilyl)propyl methacrylate (A-174, Union Carbide) was purged with nitrogen and slowly added with mixing over a 1.75 hour period to the TEOS/A-151 solution held at 140° C. After addition was complete, the solution was held at this temperature with stirring for an additional 1.5 hours. The solution was cooled to 110° C., and 1.6 parts TBEC was added. The solution was held at 110° C., with mixing for 19 hours, transferred to jars, sealed, and stored at room temperature.

A sample of this TEOS resin composition (19.5% TEOS, 394 parts) was mixed with bis(trifluoromethylsulfonyl)methane (DS) (6 parts), using sufficient heat to dissolve the DS. This was coated onto knit fiberglass fabric as in Example 3. Three 6 layer rings were made and tested as in Example 1. A ring strength of 41±1 pounds/inch (7.3±0.1 kg/cm) was found. A set time of 7 minutes was found, using the procedure of Example 5.

The above exemplifies the incorporation of vinyl triethoxysilane in the curable resin solution. Benefits include reduced cost, lower viscosity, reduced residual methacrylate monomer content, and reduced emission of methanol during cure of the resin coated sheet.

Example 9

A strip of fabric dimensioned approximately 3 inches (7.6 cm) wide and 144 inches (365.8 cm) long was cut in the machine direction from a roll of nonwoven polyester fabric known as Sontara ® polyester fabric, style 8043 (available from E. I. dupont de Nemours and Company, Textile Fibers Dept., Centre Road Bldg., Wilmington, Del.). The resin of Example 8 was coated onto this fabric strip to provide a resin content of 81.4% (weight percent) as in Example 1. The coated strip was then rolled onto a plastic core and sealed in a foil lined pouch. After six days, two six-layer test rings were prepared from the resin coated strip as in Example 1. The remainder of the resin coated strip was tested for set time as in Example 5. The set time was found to be 4.5 minutes. After 16 days at about 22° C. and about 50% relative humidity, the average ring strength of the above 6-layer rings was measured as in Example 1 and found to be 34 pounds/inch (6.1 kg/cm).

Example 10

The resin of Example 8 (163 parts) without DS catalyst was heated to 60° C. with mixing and a dry nitrogen purge. Dibutylphosphate (3.36 parts, supplied by Eastman Fine Chemicals, Rochester, N.Y.) was then added and mixed in, and then trifluoroacetic acid (1.68 parts) was added and mixed in. The resulting catalyzed resin was stored at room temperature in a sealed container. A lubricant, Pluronic ® F-108 (BASF Wyandotte Corp., Parsippany, N.J.) (7 parts), was added to the catalyzed resin with mixing, a nitrogen purge, and sufficient heat to essentially dissolve the Pluronic ® into the resin.

Two strips of Sontara ® 8043 fabric of Example 9 dimensioned approximately 3 inches (7.6 cm) wide, 144 inches (365.8 cm), and 96 inches (244 cm) long were cut at 30° from the machine direction of the roll of the fabric. The above resin was coated onto each strip of fabric and stored as in Example 1, resulting in resin contents of 82.5% and 82.6% (weight percent), respectively, to form two individual rolls of pre-lubricated sheet material.

Two 2 inch (5.1 cm) diameter mandrels were covered with a layer of 1 inch (2.5 cm) thick open celled polyether urethane foam (supplied by Illbruck USA, Minneapolis, Minn.) which in turn was covered with a layer of 3 inch (7.6 cm) polyester stockinet (MS03, 3M Company, St. Paul, Minn.). A thermocouple was placed on the surface of each of these, and synthetic (polyester) cast padding (MW03, 3M Company) was spirally wrapped over the stockinet surface and covering the thermocouples with two layers. The initial temperature of each was recorded and the mean value is shown in Table 2. The above 144 inch (365.8 cm) length of coated 8043 fabric was removed from the sealed pouch, submerged in 23° C. water, squeezed three times, removed from the water and squeezed again to remove excess water. The water activated material was then wrapped onto each covered mandrel to 6 layers with the end of the thermocouple centered under the wraps. The material unwound easily without sticking to the gloves of the applier. The cylinder formed could be rubbed over its entire length, without sticking to the gloves and the layers did not separate from each other. The temperature was recorded at 30 second intervals starting at 2.5 minutes after the coated 8043 fabric was submerged in water. The maximum temperature reached is shown in Table 2. This indicates that essentially no exotherm occurs with this material.

The above 96 inch (244 cm) length of pre-lubricated coated Sontara 8043 fabric was removed from the sealed pouch in a dry room (relative humidity <6%) and cut into five 19 inch (48 cm) lengths which were then individually sealed in foil lined pouches. The procedure described in U.S. Pat. No. 4,667,661, which is incorporated herein by reference, for determining the coefficient of friction of casting tapes was followed with one exception. An MTS$_R$ Sintech TestWorks ® advanced software for materials testing version 2.1 (MTS Systems, Corp. Research Triangle Park, N.C.) on a Dell 486P 33 (Dell Computer Corp, Austin, Tex.) was used in place of the Microcon II microprocessor to calculate the average tension force on each of the five samples. The mean kinetic coefficient of friction was found to be 0.25.

Example 11

For comparative purposes two strips of Sontara ® 8043 fabric were prepared, coated, and stored as in Example 10 using a water curable, isocyanate functional, polyurethane prepolymer resin described in Example 1 of European patent application EP 486020, published May 20, 1992. Resin contents of 82.4% and 82.7% were obtained on the 144 inch (365.8 cm) and 96 inch (244 cm) strips, respectively.

The temperature reached during water cure under 6 layers was measured as in Example 10 and is shown in Table 2. This indicates that a greater exotherm occurs with this conventional material compared with that of Example 10. The mean kinetic coefficient of friction was determined as in Example 10 and found to be 0.25.

TABLE 2

| Example | $T_1$ (°C.) | $T_{max}$ (°C.) | $t_{max}$ (min) |
|---------|-------------|-----------------|-----------------|
| 10      | 21.5        | 22              | 2.5             |
| 11      | 21.5        | 31.5            | 5               |

$T_1$ = initial temperature under padding and casting material
$T_{max}$ = maximum temperature reached under padding and casting material
$t_{max}$ = time at which $T_{max}$ was reached The following table is an expansion of the data in Table 2 showing a full time/temperature profile for the materials of Examples 10 and 11.

TABLE 3

| Time (min) | T (°C.) Example 10 | T (°C.) Example 11 |
|------------|---------------------|---------------------|
| 0          | 21.5                | 21.5                |
| 1          |                     | 22                  |
| 1.5        |                     | 22.5                |
| 2          |                     | 24                  |
| 2.5        | 22                  | 25                  |
| 3          | 22                  | 27.5                |
| 3.5        | 22                  | 29                  |
| 4          | 22                  | 30.5                |
| 4.5        | 22                  | 31                  |
| 5          | 21.5                | 31.5                |
| 5.5        | 21.5                | 31                  |
| 6          | 21                  | 31                  |
| 6.5        | 21                  | 31                  |
| 7          | 21                  | 30                  |
| 7.5        | 20.5                | 29                  |
| 8          | 20                  |                     |
| 8.5        | 20                  |                     |
| 9          | 20                  |                     |
| 9.5        | 19.5                |                     |
| 10         | 19.5                |                     |
| 11         | 19.5                |                     |
| 12         | 19                  |                     |
| 13         | 18.5                |                     |
| 14         | 18.5                |                     |
| 15         | 18.5                |                     |
| 16         | 18.5                |                     |
| 17         | 18.5                |                     |
| 18         | 18.5                |                     |
| 19         | 18                  |                     |
| 20         | 18.5                |                     |
| 40         | 18                  |                     |
| 60         | 18                  |                     |
| 80         | 19                  |                     |

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An orthopedic support material comprising:
   (a) a water-curable resin composition comprising:
      (i) a water-reactive liquid organometallic compound having at least one hydrolyzable group per molecule and a viscosity of no greater than about 100,000 centipoise under ambient conditions; and
      (ii) an organic polymer, having a number average molecular weight of at least about 400, mixed with the water-reactive liquid organometallic compound; and
   (b) a flexible substrate coated with the water-curable resin composition.

2. The orthopedic support material of claim 1 wherein the resin composition is stable at a temperature of about 0°–40° C. and is capable of curing upon exposure to water to form a support material at a temperature of about 10°–100° C.

3. The orthopedic support material of claim 2 wherein the water-curable resin composition is capable of curing at a temperature of about 20°–50° C.

4. The orthopedic support material of claim 2 wherein the resin composition is capable of curing at a temperature of about 20°–30° C.

5. The orthopedic support material of claim 1 wherein the resin composition is capable of curing upon exposure to water without the generation of substantial heat.

6. The orthopedic support material of claim 1 wherein the water-curable resin composition has a viscosity of about 5,000–500,000 centipoise under ambient conditions.

7. The orthopedic support material of claim 1 wherein the organic polymer is dissolved within the water-reactive liquid organometallic compound.

8. The orthopedic support material of claim 1 wherein the water-curable resin composition contains substantially no organic solvent.

9. The orthopedic support material of claim 1 wherein the viscosity of the liquid organometallic compound is no greater than about 3,000 centipoise.

10. The orthopedic support material of claim 1 wherein the water-reactive liquid organometallic compound is a compound of the formula $(R^1O)_xMR^2_{(y-x)}$ wherein:
   (a) each $R^1$ is independently a substituted or unsubstituted $C_1$–$C_{100}$ hydrocarbon group, optionally interrupted in the backbone by 1–50 nonperoxide —O—, —S—, —C(O)—, or —N— groups;
   (b) each $R^2$ is independently selected from the group consisting of hydrogen and a substituted or unsubstituted $C_1$–$C_{100}$ hydrocarbon group, optionally interrupted in the backbone by 1–50 nonperoxide —O—, —S—, —C(O)—, or —N— groups;
   (c) x is an integer between 1 and y, inclusive;
   (d) y is the valence of M; and
   (e) M is selected from the group consisting of boron, aluminum, silicon, and titanium.

11. The orthopedic support material of claim 10 wherein y=x.

12. The orthopedic support material of claim 10 wherein:
   (a) each $R^1$ is independently selected from the group consisting of a $C_1$–$C_{20}$ alkyl, a $C_3$–$C_{18}$ cycloalkyl, a $C_6$–$C_{18}$ aryl, and a $C_1$–$C_{18}$ acyl; and
   (b) each $R^2$ is independently selected from the group consisting of hydrogen, a $C_1$–$C_{20}$ alkyl, a $C_3$–$C_{18}$ cycloalkyl, a $C_6$–$C_{18}$ aryl, and a $C_2$–$C_{18}$ alkenyl.

13. The orthopedic support material of claim 12 wherein each $R^2$ is independently selected from the group consisting of hydrogen, methyl, ethyl, phenyl, and vinyl.

14. The orthopedic support material of claim 13 wherein the water-reactive liquid organometallic compound is tetraethoxysilane.

15. The orthopedic support material of claim 1 wherein the organic polymer has a number average molecular weight of about 4,000–30,000.

16. The orthopedic support material of claim 1 wherein the water-curable resin composition further includes an effective amount of an acid catalyst.

17. The orthopedic support material of claim 1 wherein the water-reactive liquid organometallic compound has at least three hydrolyzable groups per molecule.

18. An orthopedic support material comprising:
   (a) a water-curable resin composition comprising:
      (i) a water-reactive liquid organometallic compound of the formula $(R_1O)_xMR^2_{(y-x)}$ wherein:
         (A) each $R^1$ is independently selected from the group consisting of a $C_1$–$C_8$ alkyl, a $C_5$–$C_8$ cycloalkyl, a $C_6$–$C_{10}$ aryl, and a $C_1$–$C_8$ acyl; and
         (B) each $R^2$ is independently selected from the group consisting of hydrogen, a $C_1$–$C_{10}$ alkyl, a $C_5$–$C_8$ cycloalkyl, a $C_6$–$C_{10}$ aryl, and a $C_2$–$C_{10}$ alkenyl;
      (ii) an effective amount of a catalyst; and
      (iii) an organic polymer, having a number average molecular weight of at least about 400, mixed with the water-reactive liquid organometallic compound; and
   (b) a flexible substrate impregnated with the water-curable resin composition.

19. The orthopedic support material of claim 18 wherein the resin composition further includes a filler.

20. The orthopedic support material of claim 19 wherein the filler is calcium metasilicate.

21. The orthopedic support material of claim 18 wherein the organic polymer is a nonreactive polymer.

22. The orthopedic support material of claim 21 wherein the nonreactive organic polymer is blended with a second dissimilar polymer.

23. The orthopedic support material of claim 18 wherein the organic polymer is an addition polymer derived from at least one type of ethylenically unsaturated monomer.

24. The orthopedic support material of claim 23 wherein the ethylenically unsaturated monomer is selected from the group consisting of butadiene, styrene, isobutyl methacrylate, maleic anhydride, vinyl triethoxysilane, 3-(trimethoxysilyl)propyl methacrylate, and mixtures thereof.

25. The orthopedic support material of claim 18 wherein the catalyst is an acid catalyst.

26. The orthopedic support material of claim 25 wherein the catalyst is selected from the group consisting of an alkane sulfonic acid, a perfluorocarboxylic acid, a bis(perfluoroalkylsulfonyl)methane, a dialkyl phosphate, and mixtures thereof.

27. The orthopedic support material of claim 18 wherein the organic polymer is a condensation polymer.

28. The orthopedic support material of claim 27 wherein the condensation polymer is an alkoxy silane-functional organic polymer.

29. A cured orthopedic support comprising a substrate impregnated with crosslinked metal oxide regions, wherein the metal is selected from the group consisting of Si, Ti, Al, and B, intertwined with organic polymeric regions.

30. A water-curable resin-coated sheet comprising:
   (a) a water-curable resin composition comprising:
      (i) a water-reactive liquid organometallic compound having at least one hydrolyzable group per molecule and a viscosity of no greater than about 100,000 centipoise under ambient conditions;
      (ii) an organic polymer, having a number average molecular weight of at least about 400, mixed with the water-reactive liquid organometallic compound; and
      (iii) an effective amount of a catalyst; and
   (b) a flexible substrate impregnated with the water-curable resin composition.

31. The water-curable resin-coated sheet of claim 30 wherein the polymer is an addition polymer.

32. A method of preparing an orthopedic support material comprising impregnating a flexible substrate with a water-curable resin composition comprising:
   (a) a water-reactive liquid organometallic compound having at least one hydrolyzable group per molecule; and
   (b) an organic polymer, having a number average molecular weight of at least about 400, mixed with the water-reactive liquid organometallic compound.

33. The method of claim 32 wherein the water-curable resin composition is prepared by dissolving the organic polymer in the water-reactive liquid organometallic compound.

34. The method of claim 33 wherein the step of dissolving the polymer in the liquid organometallic compound includes mixing the organic polymer and the liquid organometallic compound and heating the mixture at a temperature of about 80°–160° C.

35. The method of claim 32 wherein the water-curable resin composition is prepared by:
   (a) dissolving the organic polymer in an organic solvent having a boiling point lower than that of the liquid organometallic compound;
   (b) diluting the solution of the organic polymer in the organic solvent with the liquid organometallic compound; and
   (c) removing the organic solvent.

36. The method of claim 35 wherein the step of removing the organic solvent includes a step of heating the solution of organic polymer, organometallic compound, and organic solvent at a temperature of about 80°–120° C.

37. The method of claim 32 wherein the water-curable resin composition is prepared by:
   (a) adding at least one type of monomer to the liquid organometallic compound; and
   (b) adding a polymerization initiator to the mixture of monomer and liquid organometallic compound to convert the monomer to polymer.

38. The method of claim 37 further including a step of heating the mixture of monomer, liquid organometallic compound, and polymerization initiator at a temperature of about 70°–140° C.

* * * * *

UNITED STATES PATENT AND TRADEMARK OFFICE
CERTIFICATE OF CORRECTION

PATENT NO. : 5,364,693

DATED : November 15, 1994

INVENTOR(S) : Dean M. Moren and Dean A. Ersfeld

It is certified that error appears in the above-indentified patent and that said Letters Patent is hereby corrected as shown below:

Col. 15 lines 4-5, insert -- ® -- after "Pluronic".

Col. 21, line 59, insert -- be -- before "about".

Col. 23, line 13, "TEES" should read -- TEOS --.

Col. 25, line 62, insert -- ® -- after "Sontara".

Signed and Sealed this

Twenty-eighth Day of November 1995

Attest:

BRUCE LEHMAN

Attesting Officer

Commissioner of Patents and Trademarks